United States Patent
Wright, III

(10) Patent No.: US 10,758,329 B1
(45) Date of Patent: Sep. 1, 2020

(54) HYDRATING MOUTH GUARD

(71) Applicant: Raymond L. Wright, III, Chicago, IL (US)

(72) Inventor: Raymond L. Wright, III, Chicago, IL (US)

( * ) Notice: Subject to any disclaimer, the term of this patent is extended or adjusted under 35 U.S.C. 154(b) by 0 days.

(21) Appl. No.: 16/545,254

(22) Filed: Aug. 20, 2019

(51) Int. Cl.
| | |
|---|---|
| *A61C 19/06* | (2006.01) |
| *A61B 5/00* | (2006.01) |
| *A61L 31/14* | (2006.01) |
| *A61B 5/053* | (2006.01) |
| *A61M 37/00* | (2006.01) |
| *A61B 5/145* | (2006.01) |
| *A63B 71/08* | (2006.01) |
| *A61N 1/32* | (2006.01) |

(52) U.S. Cl.
CPC .......... *A61C 19/063* (2013.01); *A61B 5/0537* (2013.01); *A61B 5/14532* (2013.01); *A61B 5/4839* (2013.01); *A61B 5/4875* (2013.01); *A61B 5/682* (2013.01); *A61L 31/145* (2013.01); *A61M 37/0092* (2013.01); *A61N 1/325* (2013.01); *A63B 71/085* (2013.01); *A61B 2562/0285* (2013.01); *A61M 2205/3569* (2013.01)

(58) Field of Classification Search
CPC ....... A61C 19/063; A61C 7/08; A61L 31/145; A61M 37/0092; A61M 2205/3569; A61N 1/325; A61F 5/566; A61F 5/56; A61F 2005/563; A61F 5/58; A61B 5/0537; A61B 5/14532; A61B 5/4839; A61B 5/4875; A61B 5/682; A61B 2562/0285; A61B 5/4547; A61B 5/4552; A61B 5/4557; A61B 5/0534; A63B 71/085; A63B 2071/086; A63B 2017/088

USPC .................. 128/861, 859; 604/66, 20; 433/6
See application file for complete search history.

(56) References Cited

U.S. PATENT DOCUMENTS

| | | | |
|---|---|---|---|
| 4,141,359 | A | 2/1979 | Jacobsen et al. |
| 4,517,173 | A | 5/1985 | Kizawa et al. |
| (Continued) | | | |

FOREIGN PATENT DOCUMENTS

| | | |
|---|---|---|
| CA | 2067133 | 7/1998 |
| KR | 100328654 | 3/2002 |

OTHER PUBLICATIONS

Schmitt, Julie: "Hydrating Mouth Guard Could Be a Game Changer" (Year: 2016).*

(Continued)

*Primary Examiner* — Kari K Rodriquez
*Assistant Examiner* — Caitlin A Carreiro
(74) *Attorney, Agent, or Firm* — Fish & Richardson P.C.

(57) ABSTRACT

A transmucosal delivery device includes a mouthpiece configured for receipt on a user's teeth, a permeable member coupled to the mouthpiece, a measurement module coupled to the mouthpiece for monitoring hydration of the user, and an excitation module coupled to the mouthpiece for inducing release of a hydrating substance from the permeable member based on the monitored hydration. The hydrating substance is delivered to the user through the user's oral mucosal tissue. Alternatively, a permeable member of a transmucosal delivery device houses an insulin solution to be delivered to the user through the user's oral mucosal tissue, and a measurement module coupled to the mouthpiece for monitoring blood glucose concentration of the user.

16 Claims, 11 Drawing Sheets

(56) References Cited

U.S. PATENT DOCUMENTS

| | | | |
|---|---|---|---|
| 4,540,566 | A | 9/1985 | Davis et al. |
| 4,572,832 | A | 2/1986 | Kigasawa et al. |
| 4,619,935 | A | 10/1986 | Robison |
| 4,642,903 | A | 2/1987 | Davies |
| 4,713,243 | A | 12/1987 | Schiraldo et al. |
| 4,761,288 | A | 8/1988 | Mezei et al. |
| 4,829,056 | A | 5/1989 | Sugden |
| 4,900,552 | A | 2/1990 | Sanvordeker et al. |
| 4,900,554 | A | 2/1990 | Yanagibashi et al. |
| 4,937,078 | A | 6/1990 | Mezei et al. |
| 5,021,053 | A | 6/1991 | Barclay et al. |
| 5,059,421 | A | 10/1991 | Loughrey et al. |
| 5,114,719 | A | 5/1992 | Sabel et al. |
| 5,137,729 | A | 8/1992 | Kuroya et al. |
| 5,197,882 | A | 3/1993 | Jernberg |
| 5,200,194 | A | 4/1993 | Edgren et al. |
| 5,200,195 | A | 4/1993 | Dong et al. |
| 5,225,212 | A | 7/1993 | Martin et al. |
| 5,248,310 | A | 9/1993 | Barclay et al. |
| 5,267,862 | A | 12/1993 | Parker |
| 5,320,840 | A | 6/1994 | Camble et al. |
| 5,326,685 | A | 7/1994 | Gaglio et al. |
| 5,713,852 | A | 2/1998 | Anthony et al. |
| 5,741,500 | A | 4/1998 | Yates |
| 5,762,952 | A | 6/1998 | Barnhart et al. |
| 5,780,045 | A | 7/1998 | McQuinn et al. |
| 5,849,322 | A | 12/1998 | Ebert et al. |
| 5,855,908 | A | 1/1999 | Stanley et al. |
| 5,874,095 | A | 2/1999 | Deckner et al. |
| 5,891,465 | A | 4/1999 | Keller et al. |
| 6,048,545 | A | 4/2000 | Keller et al. |
| 6,319,510 | B1 | 11/2001 | Yates |
| 7,122,012 | B2 | 10/2006 | Bouton et al. |
| 7,971,591 | B2 | 7/2011 | Jansheski |
| 8,205,618 | B2 | 6/2012 | Berghash et al. |
| 9,549,841 | B2 | 1/2017 | Hermanson et al. |
| 9,770,354 | B2 | 9/2017 | Bardach et al. |
| 9,815,838 | B2 | 11/2017 | Moran et al. |
| 9,901,561 | B2 | 2/2018 | Heller et al. |
| 9,927,391 | B2 | 3/2018 | Tran |
| 10,029,015 | B2 | 7/2018 | Hersel et al. |
| 2004/0025887 | A1 | 2/2004 | Scopton |
| 2004/0158194 | A1* | 8/2004 | Wolff ............ A61C 19/063 604/66 |
| 2006/0002994 | A1 | 1/2006 | Thomas et al. |
| 2010/0286587 | A1 | 11/2010 | Gross |
| 2011/0186055 | A1 | 8/2011 | Makkar et al. |
| 2011/0209714 | A1 | 9/2011 | Makkar et al. |
| 2011/0234240 | A1* | 9/2011 | Yager ............ A61B 5/4875 324/634 |
| 2011/0297165 | A1 | 12/2011 | Wang et al. |
| 2013/0018069 | A1 | 1/2013 | Friedman et al. |
| 2015/0258417 | A1* | 9/2015 | Rodgers ............ A63B 71/085 128/861 |
| 2016/0123973 | A1 | 5/2016 | Cubukcu |
| 2016/0157962 | A1* | 6/2016 | Kim ............ A61C 7/08 433/6 |
| 2018/0243635 | A1 | 8/2018 | Forrest |
| 2018/0310881 | A1 | 11/2018 | Yoon et al. |
| 2019/0054347 | A1 | 2/2019 | Saigh et al. |

OTHER PUBLICATIONS

Barbarini, Alejandro: "Study of the Effectiveness of Liposomal Oral Rehydration Solutions in an Osmotic Diarrhea Model in Rats"; American Journal of Gastroenterology: vol. 112, supplement 1, pp. 5590-5591: Oct. 2017 (Year: 2017).*

Kapoor, et al., "Pegylated Glucose Triggered Liposomes for Insulin Delivery" Nephrology Dialysis Transplantation, , May 2018, vol. 33, Iss.suppl_1:1179-1180.

Amazon.com [online] "Under Armour UA Armourbite Mouthguard", [retrieved on Aug. 8, 2019], retrieved from URL<https://www.amazon.com/Under-Armour-ArmourBite-Mouthguard-Medium/dp/B00C1W9QIM/ref=sr_1_5?keywords=us+performance+mouth+guard&qid=1565281191&s=gateway&sr=8-5/> 7 pages.

Choudhari et al., "Liposomes as a Carrier for Oral Administration of Insulin: Effect of Formulation Factors" Journal of Microencapsulation, 1994, 11(3):319-25.

Donohoe et al., "Powering In-Body Nanosensors with Ultrasounds" IEEE Transactions on Nanotechnology, Dec. 2015, 15(2): 151-154 DOI: 10.1009/TNANO.2015.2509029.

H. M. Patel et al., "Oral Administration of Insulin by Encapsulation Within Liposomes" Department of Biochemistry and Chemistry, Feb. 1976, 62(1):60-63.

NeonBrite.com [online] "SportsEdge Sports Mouthpieces", [retrieved on Aug. 8, 2019], retrieved from URL<http://www.neonbrite.com/SportMain.html/> 8 pages.

PPMMouthguard.ca [online] "Pure Power Mouthguard", [retrieved on Aug. 8, 2019], retrieved from URL<https://www.ppmmouthguard.ca/types-of-ppm_s/> 1 page.

Ronald S. Sprangler "Insulin Administration Via Liposomes" Diabetes Care, 1990, 13(9):911-22.

Taniguchi et al., "Preoperative Fluid and Electrolyte Management With Oral Rehydration Therapy" Department of Anesthesiology, Kanagawa Cancer Center, 2009;23(2):222-9. doi: 10.1007/s00540-009-0743-6. Epub May 15, 2009.

Wang et al., "Piezoelectric Nanogenerators Based on Zinc Oxide Nanowire Arrays" Science, 2006, 312(5771): 242-246 DOI: 10.1126/science.1124005.

* cited by examiner

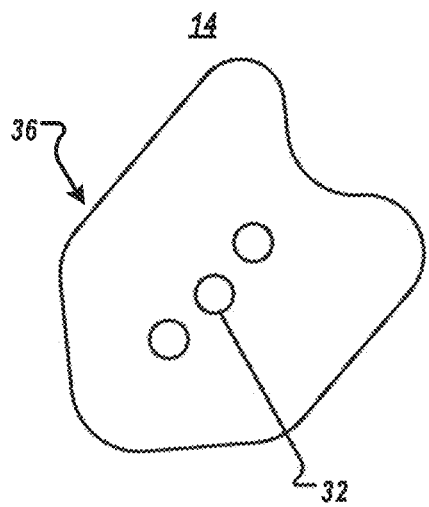
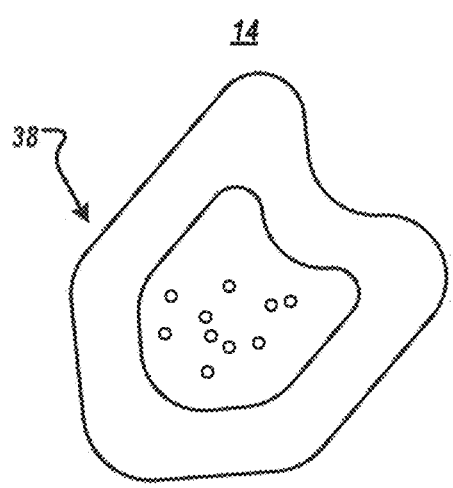
FIG. 4A                FIG. 4B
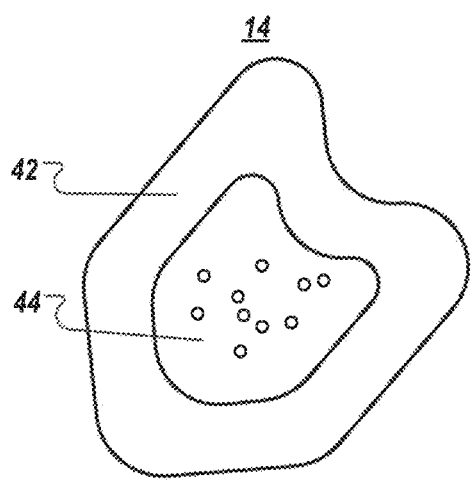
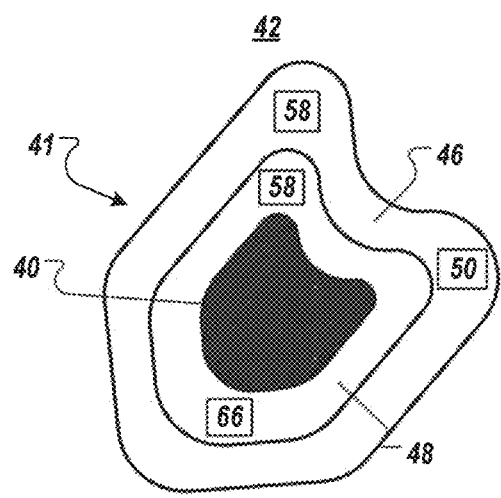
FIG. 4C                FIG. 4D
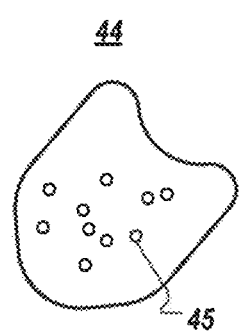
FIG. 4E

HYDRATING MOUTH GUARD

BACKGROUND

Mouth guards can be worn in an individual's mouth, covering the teeth. Mouth guards are typically designed to protect the teeth and supporting structures. Mouth guards are often worn during athletic activities.

During athletic activities, individuals may be at risk of dehydration. Dehydration can occur due to water loss from the body due to heat or exercise. Dehydration can result in decreased athletic performance and adverse health effects such as fatigue, dizziness, and dehydration sickness. The risk of dehydration can be mitigated by delivering water or other hydrating substances to an individual's bloodstream when needed.

Certain individuals may experience high blood glucose concentration levels. High blood glucose concentration levels can result in adverse health effects such as pancreatic damage and hardened blood vessels. Blood glucose concentration levels can be reduced by delivering insulin to an individual's bloodstream. Insulin improves the body's ability to absorb glucose.

SUMMARY

Medicinal and nutritional substances, including hydrating substances and insulin, can be delivered to a user's bloodstream by various paths. Hydrating substances and insulin can be encapsulated in liposomes and delivered to a user's bloodstream through the oral mucosal tissue. Transmucosal delivery methods result in high levels of absorption in the body.

A hydrating mouth guard worn by a user to protect the user's teeth and supporting structures, particularly during athletic activities, measures the user's hydration level, and delivers hydration salts to the user via transmembrane diffusion. The mouth guard can also measure the user's blood glucose concentration and deliver an insulin solution to the user via transmembrane diffusion.

According to one aspect, a transmucosal delivery device includes a mouthpiece configured for receipt on a user's teeth and a permeable member coupled to the mouthpiece. The permeable member houses a hydrating substance to be delivered to the user through the user's oral mucosal tissue. A measurement module is coupled to the mouthpiece for monitoring hydration of the user. An excitation module is coupled to the mouthpiece for inducing release of the hydrating substance from the permeable member based on the monitored hydration.

Embodiments of this aspect may include one or more of the following features. The mouthpiece may be U-shaped. The mouthpiece may include an outer buccal surface, an inner lingual surface, and an intervening occlusal surface.

The permeable member may be in the form of a pouch housing the hydrating substance including a hydrogel. The hydrogel may include liposome-entrapped hydration salts. The hydrogel may include liposome-entrapped insulin.

The transmucosal delivery device may include a dual module including the measurement module and the excitation module. The dual module may be configured as a ring. The dual module may receive the permeable member within the perimeter of the ring. The dual module may receive the permeable member with a snap fit, with one or more magnets, and/or with one or more slide connectors.

The dual module may couple to the outer buccal surface of the mouthpiece. The dual module may be removable mounted to the mouthpiece. The dual module may couple to the mouthpiece with one or more snap fasteners, with one or more magnets, and/or with one or more slide connectors.

In some implementations, the measurement module may include one or more dielectric resonant oscillators. The excitation module may include one or more nanosensor strips configured to receive electromagnetic energy and transmit sonic energy. In some implementations, the measurement module may include a non-invasive blood glucose monitor. The excitation module may include one or more iontophoresis devices.

The transmucosal delivery device may include one or more antennas for transmitting or receiving signals. The transmucosal delivery device may include a power receiving device configured to receive electrical power from a power source. The transmucosal delivery device may include one or more batteries.

In some implementations, the mouthpiece may be configured for receipt on only the user's maxillary teeth. In some implementations, the mouthpiece may be configured for receipt on the user's maxillary teeth and mandibular teeth.

According to another aspect, a transmucosal delivery device kit includes a mouthpiece configured for receipt on a user's teeth and a permeable member housing a hydrating substance to be delivered to the user through the user's oral mucosal tissue. The transmucosal delivery device kit includes a dual module. The dual module includes a measurement module for monitoring hydration of the user and an excitation module for inducing release of the hydrating substance from the permeable member based on the monitored hydration.

Embodiments of this aspect may include one or more of the following features. The permeable member may be disposable. The transmucosal delivery device kit may include a second permeable member housing a hydrating substance to be delivered to the user through the user's oral mucosal tissue.

The dual module may be configured as a ring. The dual module may receive the permeable member within the perimeter of the ring. The dual module may receive the permeable member with a snap fit, with one or more magnets, and/or with one or more slide connectors. The dual module may couple to an outer buccal surface of a U-shaped mouthpiece. The dual module may be removable mounted to the mouthpiece. The mouthpiece may be configured for receipt on only the user's maxillary teeth. The mouthpiece may be configured for receipt on the user's maxillary teeth and mandibular teeth.

According to another aspect, a method of transmucosal delivery includes monitoring hydration of a user using a measurement module coupled to a mouthpiece. The method includes releasing a hydrating substance from a permeable member coupled to the mouthpiece based on the monitored hydration such that the hydrating substance is absorbed transmucosally via the user's mouth.

Embodiments of this aspect may include one or more of the following features. The method of transmucosal delivery may include transmitting, to a computing system, data indicating the hydration of the user; and receiving, from the computing system, a signal that causes the permeable member to release the hydrating substance. The method may include ceasing release of the hydrating substance from the permeable member coupled to the mouthpiece based on the monitored hydration. The method may include transmitting, to a computing system, data indicating the hydration of the user; and receiving, from the computing system, a signal that causes the permeable member to cease releasing the hydrating substance. Releasing the hydrating substance from the permeable member may include sonication of the hydrating substance.

According to another aspect, a transmucosal delivery device includes a mouthpiece configured for receipt on a user's teeth and a permeable member coupled to the mouthpiece. The permeable member houses an insulin solution to be delivered to the user through the user's oral mucosal tissue. A measurement module is coupled to the mouthpiece for monitoring blood glucose concentration of the user. An excitation module is coupled to the mouthpiece for inducing release of the insulin solution from the permeable member based on the monitored blood glucose concentration.

According to another aspect, a transmucosal delivery device kit includes a mouthpiece configured for receipt on a user's teeth and a permeable member housing an insulin solution to be delivered to the user through the user's oral mucosal tissue. The transmucosal delivery device kit includes a dual module. The dual module includes a measurement module for monitoring blood glucose concentration of the user, and an excitation module for inducing release of the insulin solution from the permeable member based on the monitored blood glucose concentration.

In another aspect, a method of transmucosal delivery includes monitoring blood glucose concentration of a user using a measurement module coupled to a mouthpiece. The method includes releasing an insulin solution from a permeable member coupled to the mouthpiece based on the monitored blood glucose concentration such that the insulin solution is absorbed transmucosally via a user's mouth.

Embodiments of this aspect may include one or more of the following features. The method of transmucosal delivery may include transmitting, to a computing system, data indicating the blood glucose concentration of the user. The method may include receiving, from the computing system, a signal that causes the permeable member to release the insulin solution. The method may include ceasing release of the insulin solution from the permeable member coupled to the mouthpiece based on the monitored blood glucose concentration. Releasing the insulin solution from the permeable member may include iontophoresis of the insulin solution.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 4A-4E are diagrams showing the components of the side lobe of the hydrating mouth guard.

DETAILED DESCRIPTION

Figure 1:
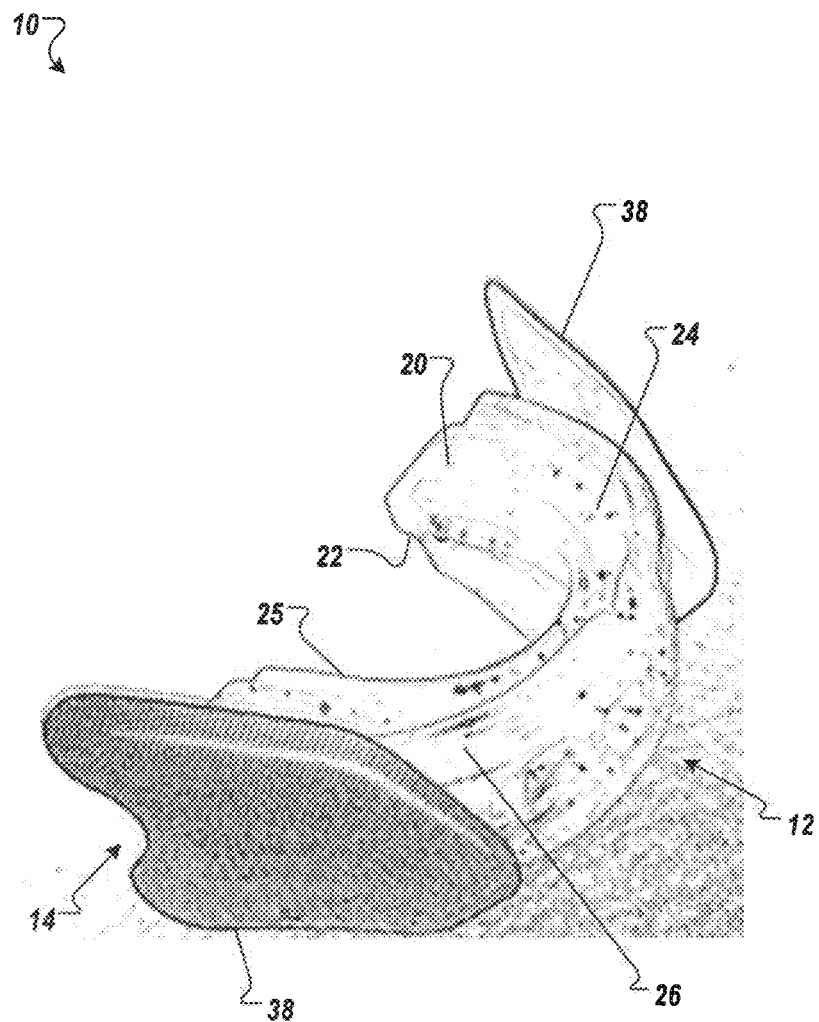
FIG. 1 is a diagram of an example hydrating mouth guard.
Figure 2:
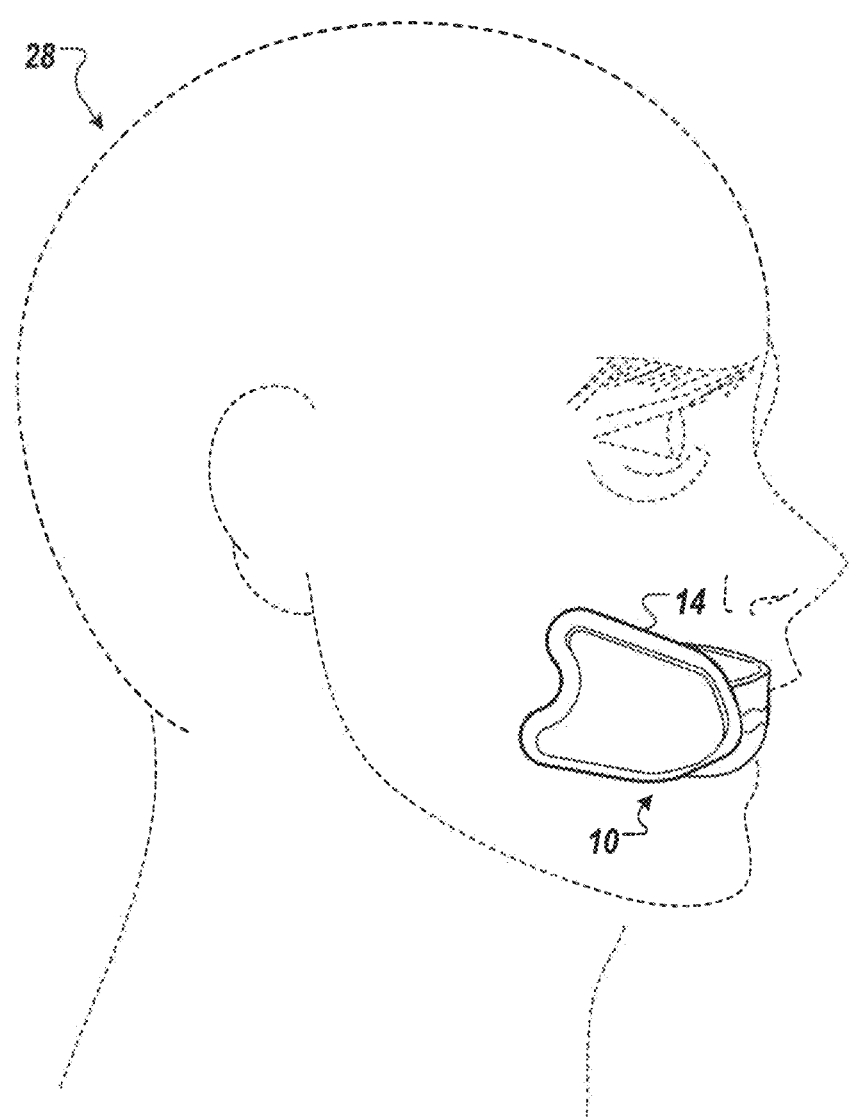
FIG. 2 is a diagram of an example environment for using a hydrating mouth guard.
Figure 3A:
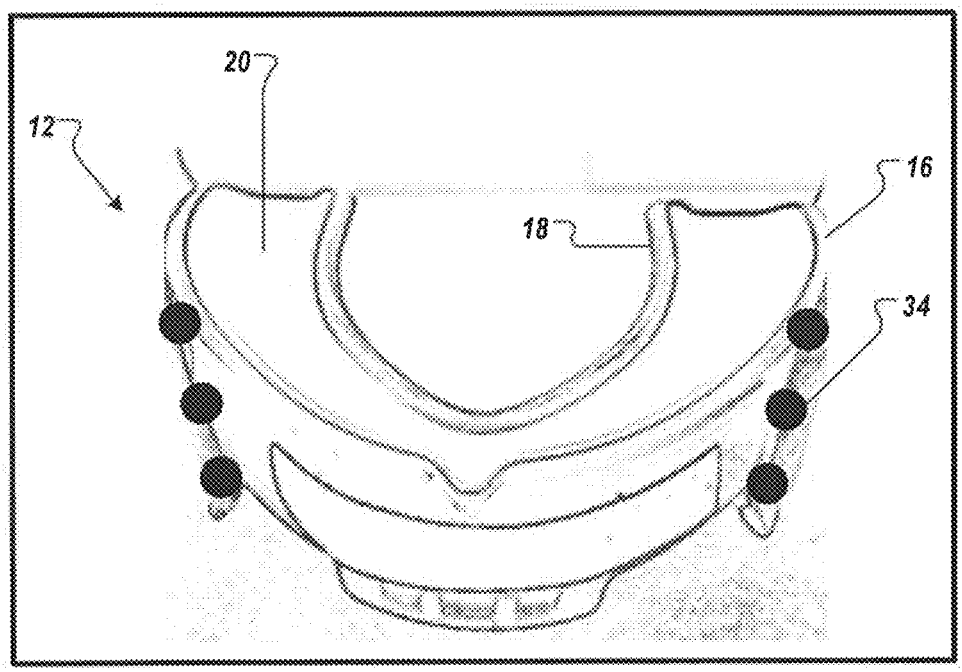
FIGS. 3A-3F are various perspective views of the hydrating mouth guard.
Figure 3B:
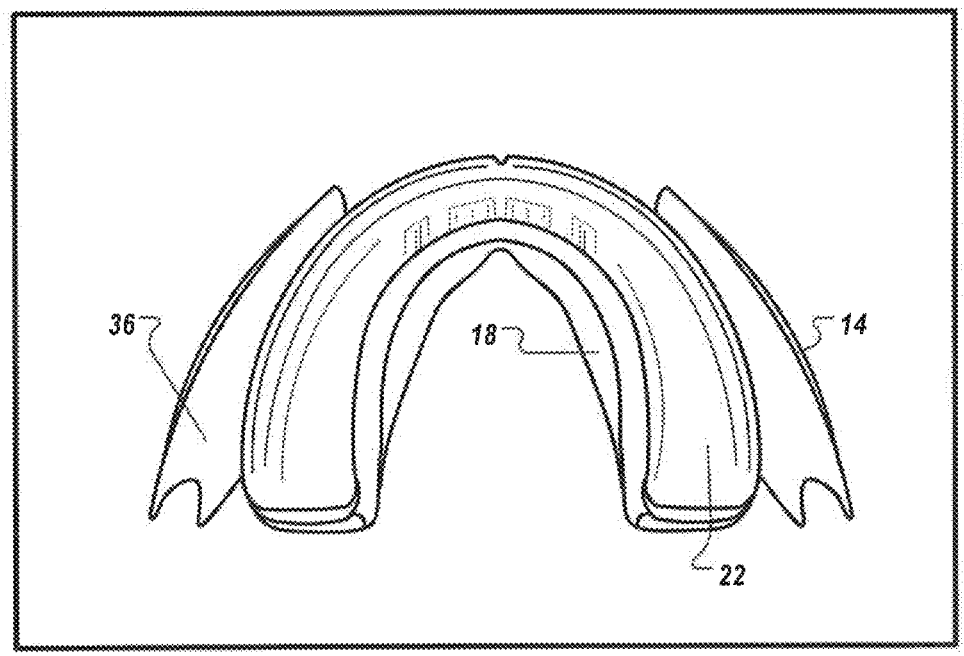
Figure 3C:
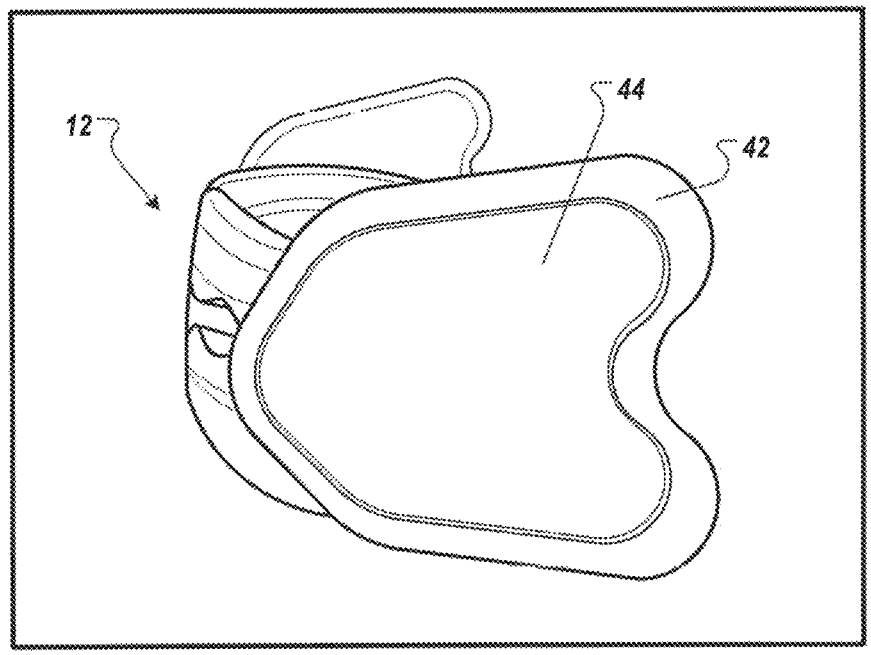
Figure 3D:
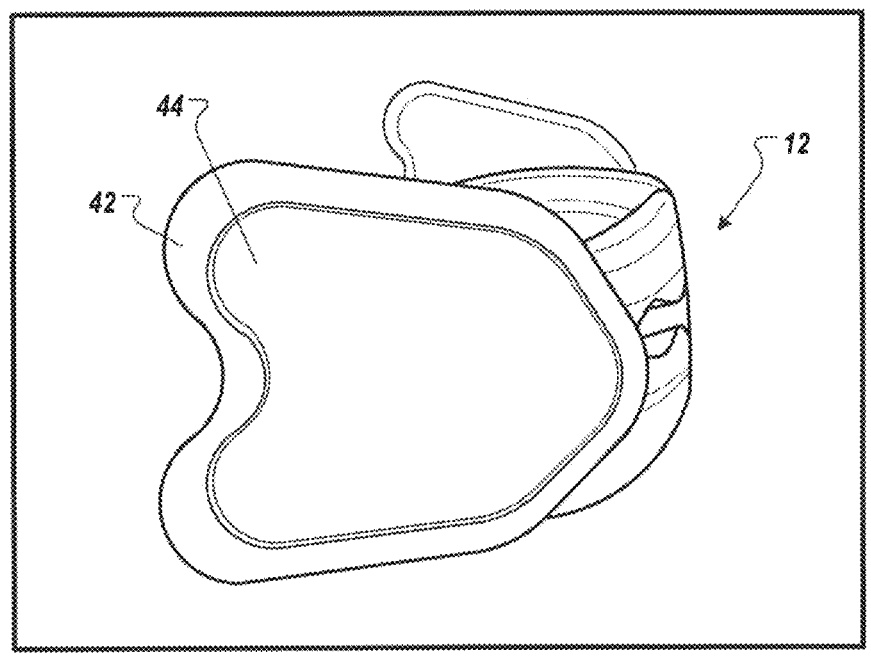
Figure 3E:
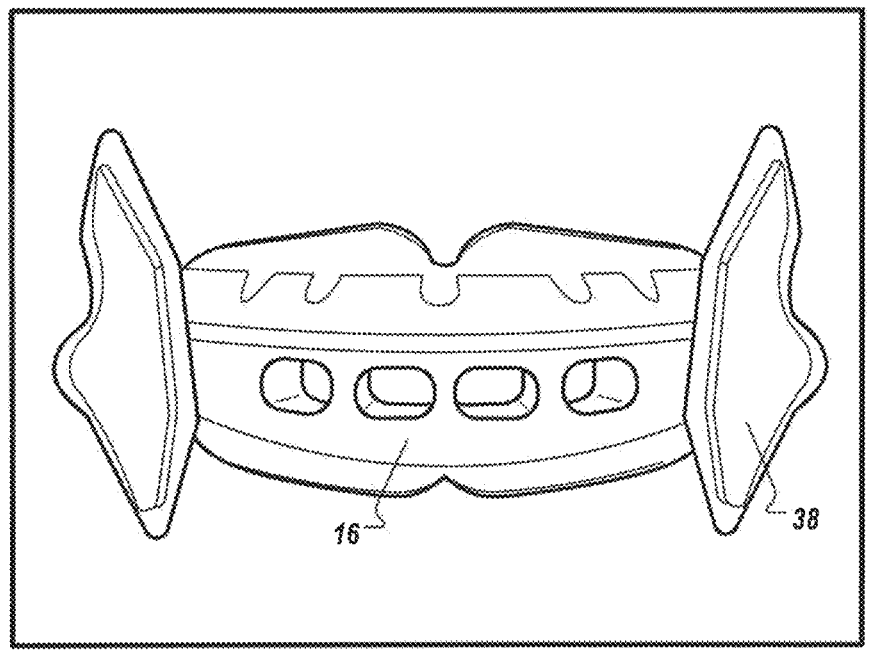
Figure 3F:
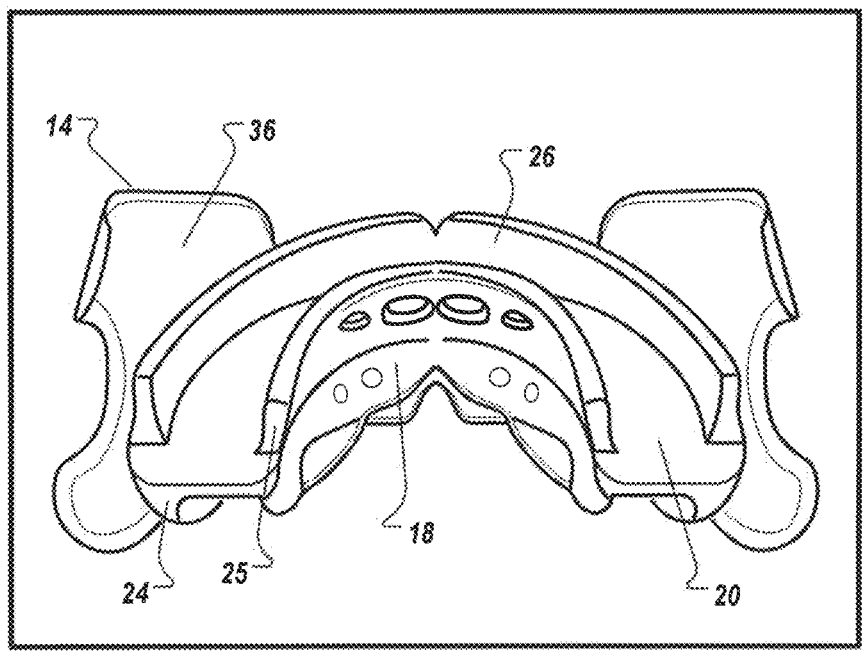

Referring to FIGS. 1 and 2, a hydrating mouth guard 10 worn by a user 28 to protect the user's teeth and supporting structures, particularly during athletic activities, measures the user's hydration level, and delivers hydration salts to the user 28 via transmembrane diffusion. The mouth guard 10 includes a U-shaped mouthpiece 12 designed to fit on a user's teeth, and two side lobes 14 removably attached to the mouthpiece 12 that, in use, are positioned against the buccosal tissue of the user's inner cheeks. The side lobes 14 include components, discussed below, for monitoring the hydration level of the user 28 and inducing release of a hydrating substance from the side lobes 14 to the buccosal tissue.

Referring to FIGS. 3A-3F, the mouthpiece 12 includes an outer portion 26 having an outer surface 16, an inner portion 25 having an inner surface 18, and a mid-portion 24 having top and bottom intervening surfaces 20, 22. When worn by the user 28, the outer portion 26 covers the outer surfaces of the teeth with the outer surface 16 positioned facing the buccosal tissue and exterior surfaces 38 of the side lobes 14 positioned against the user's inner cheeks. The inner portion 25 covers the surfaces of the teeth that face the tongue, and the intervening surfaces 20, 22 of the mid-portion 24 cover the grinding surfaces of the upper and lower teeth, respectively.

The mid-portion 24 of the mouthpiece 12 is made of a soft and moldable material, and the inner and outer portions 25, 26, and the side lobes 14 are made of a harder material. The mid-portion 24 of the mouthpiece 12 can be molded to fit the teeth of the user 28. For example, the mouthpiece 12 can be molded to fit the teeth using a custom dental impression or 3D scan, or by heating or boiling the mouthpiece 12 before pressing the mouth guard 10 onto the user's teeth. The mid-portion 24 can be made with thermoplastic materials such as ethylene-vinyl acetate rubber or soft polyurethane. The inner and outer portions 25, 26, and the side lobes 14 can be made with materials such as a rigid acrylic, thermoplastic ethylene-vinyl acetate copolymer, clear thermoplastic, laminated thermoplastic, or hard polyurethane.

The mouthpiece 12 includes one or more mechanisms, for example, one or more snap fasteners 34, on the outer surface 16 for attaching the side lobes 14 to the mouthpiece 12. Referring to FIGS. 4A-4B, the side lobes 14 each have an interior surface 36 that faces the mouthpiece 12 with one or more mechanisms, for example, one or more corresponding snap fasteners 32 on the interior surface 36 that cooperate with fasteners 34 to removably attach the side lobes 14 to the mouthpiece 12. Alternatively, the side lobes 14 connect to the outer surface 16 of the mouthpiece 12 using, for example, one or more magnets, or one or more slide connectors.

Referring to FIGS. 4C-4E, each side lobe 14 includes a dual module 42 for controlling release of a hydrating substance, and a permeable member 44 housing the hydrating substance. The dual module 42 is formed as a ring 41. The ring 41 can be any appropriate shape, for example, oblong, round, "D" shaped, or chevron shaped. The dual module 42 can be made with materials such as a biomedical medical grade plastic or amorphous thermoplastic with dielectric properties. The permeable member 44 is made of a polymeric material encapsulating a hydrogel material. The dual module 42 removably receives the permeable member 44 within the inner perimeter 40 of the ring 41 via, for example, a snap fit. Alternatively, the dual module 42 removably receives the permeable member 44 using, for example, one or more magnets, or one or more slide connectors.

The dual module 42 includes a measurement module 46 for monitoring the hydration level of the user, and an excitation module 48 for inducing release of a hydrating substance from the permeable member 44.

Figure 5:
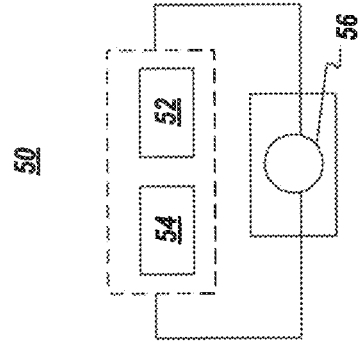
FIG. 5 is a diagram of a dielectric resonant oscillator.

Referring to FIG. 5, the measurement module 46 can include one or more dielectric resonant oscillators 50 for measuring hydration. The dielectric resonant oscillators 50 include a radio frequency emitter 52, a sensor 54, and a microstrip ring resonator 56.

Figure 6:
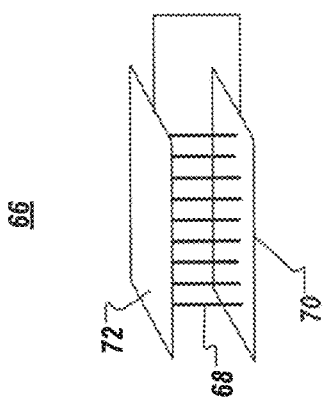
FIG. 6 is a diagram of a nanosensor strip.

Referring to FIG. 6, the excitation module 48 can include one or more nanosensor strips 66. The nanosensor strips 66 include piezoelectric nanowires 68 extending between two electrodes 70, 72. The nanosensor strips 66 can receive electrical energy at the electrode 70, and transmit ultrasonic energy from the electrode 72, to perform sonication on the permeable member 44. Sonication is the act of applying sonic energy to agitate particles in a sample, as described in U.S. Patent Application No. 2006/0002994, hereby incorporated by reference in its entirety.

The permeable member 44 contains the hydrating substance to be delivered to the user 28 through the mucosal tissue. The permeable member 44 is in the form of a pouch that contains a hydrogel. The composition of the hydrogel is described in U.S. Pat. No. 10,029,015, hereby incorporated by reference in its entirety. The hydrogel is a polymeric prodrug composition with a plurality of pores with openings on its surface.

The porous hydrogel contains liposomes 45. The composition of the liposomes 45 is described in Canadian Patent No. CA2067133, hereby incorporated by reference in its entirety. The liposomes 45 are nano-sized, e.g., between 0.1 and 0.4 microns, hollow bubbles made of phospholipids. The phospholipids are amphipathic, that is, part of their structure is water-soluble, or hydrophilic, and the other part is fat-soluble, or hydrophobic. When added to water, the water-soluble part of the phospholipid interacts with the water, and the fat-soluble part of the molecule avoids the water. The water-soluble part of the molecule can carry encapsulated nutrients through the membrane of the cell wall to provide direct inter-cellular nutrition. The properties of the liposomes 45 allow the encapsulated nutrients to retain full potency until they are absorbed by the cells where needed. The liposomes 45 can have a positive or negative surface charge to enhance their penetration using iontophoresis.

The liposomes 45 can encapsulate hydration salts. An example hydration salt formula is the World Health Organization (WHO) formula for reduced osmolarity oral rehydration salts. The formula is 2.6 grams (0.092 oz) salt (NaCl), 2.9 grams (0.10 oz) trisodium citrate dihydrate ($C_6H_5Na_3O_7.2H_2O$), and 1.5 grams (0.053 oz) potassium chloride (KCl), and 13.5 grams (0.48 oz) anhydrous glucose ($C_6H_{12}O_6$) per liter of fluid. The formula has a total osmolarity of 243 milliosmoles per liter.

Figure 8:
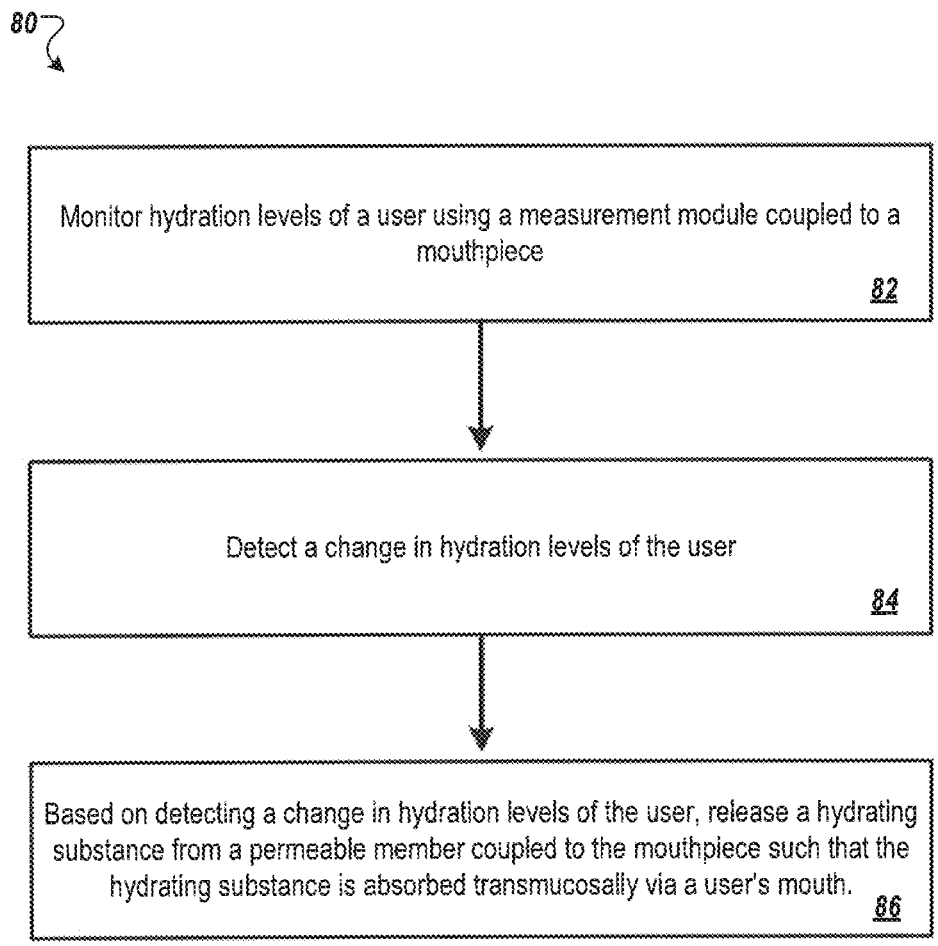
FIG. 8 is a flow diagram of a process for the hydrating mouth guard.

Referring to FIG. 8, the process 80 for the hydrating mouth guard includes monitoring hydration levels of the user using a measurement module coupled to a mouthpiece (82).

The measurement module 46 can measure hydration levels using the one or more dielectric resonant oscillators 50 that emit a scanning signal from the radio frequency emitter 52. At low frequencies, the relative permittivity of fluids in human body is dominated by the high capacitance of cell membranes, and the relative conductivity is dominated by ions in the blood plasma. At high frequencies, the cell membranes are shorted out, and conductivity is dominated by excitation and relaxation of water molecules. The conductivity is inversely proportional to hydration levels.

The process for measuring hydration levels is described in U.S. Pat. No. 7,122,012, and U.S. Patent Application No. 2011/0234240, hereby incorporated by reference in their entirety. To measure the hydration levels of the user, the scanning signal from the dielectric resonant oscillator 50 sweeps over a specified frequency range, e.g., 3 Gigahertz (GHz) to 5 GHz. The scanning signal passes through the microstrip ring resonator 56, which is in contact with the user's body tissue. The sensor 54 then receives the scanning signal and resonates in response to the scanning signal.

Characteristics of the sensor's resonance are affected by changes in the user's hydration levels. For example, the quality factor of the sensor's resonance changes when the user's hydration level changes. The dielectric resonant oscillator 50 compares the signal received by the sensor 54 to a reference signal. For example, the reference signal can correspond to the user's baseline hydration level. The difference between the received signal and the reference signal is indicative of the difference between the user's current hydration level and the user's baseline hydration level.

In some examples, the mouth guard 10 can adjust the amount of the hydrating substance released based on the level of dehydration of the user. For example, if the difference between the user's current hydration level and the user's baseline hydration level is smaller, the mouth guard 10 can release a lesser concentration of hydration salts. If the difference between the user's current hydration level and the user's baseline hydration level is larger, the mouth guard 10 can release a greater concentration of hydration salts.

The process 80 includes detecting a change in hydration level of the user (84), and based on detecting the change in hydration level of the user, releasing a hydrating substance from the permeable member coupled to the mouthpiece such that the hydrating substance is absorbed transmucosally via a user's mouth (86).

When the measurement module 46 detects a decreased hydration level of the user, the measurement module 46 sends a signal to the excitation module 48. The signal can be, for example, an electromagnetic signal operating in the radio frequency, infrared, terahertz, or optical wavebands. The electromagnetic signal stimulates the excitation module 48.

Within the excitation module 48, the nanosensor strips 66 receive the electromagnetic signal from the measurement module 46 and transmit sonic energy to perform sonication on the permeable member 44. The sonic energy can be, for example, ultrasonic energy at frequencies above 20 Kilohertz. When agitated through sonication, the hydrogel releases the liposomes 45 containing hydration salts through the membrane of the permeable member 44.

Once released from the permeable member 44, the liposomes 45 release the hydration salts via transmembrane diffusion. The hydration salts absorbs transmucosally via the user's mouth. The user's body tissues absorb the hydration salts, increasing the user's hydration level.

The method of providing hydration salts transmucosally via the user's mouth allows the hydration salts to have maximal uptake, and to deliver maximal bioeffectiveness. Providing hydration salts transmucosally avoids the disadvantages of a peroral route of delivery. When delivered perorally, bioactive nutrients and substances can be subject to interferences such as digestive system enzyme breakdown, competition for intestinal absorption, combining with other molecules, and alteration from passing through the liver. These interferences can result in low delivery of bioactive substances into the bloodstream for delivery to target tissues.

In a transmucosal delivery method, the bioactive substances adhere to the mucosal membrane, penetrate through the mucosal membrane, and diffuse through the mucosal membrane into the bloodstream. Transmucosal delivery through the oral mucosal tissue results in a higher rate of absorption directly into the bloodstream, when compared with peroral delivery.

The measurement module 46 continues to monitor the user's hydration level upon release of the hydrating substance. When the user's hydration level rises to reach a pre-determined level, the measurement module 46 ceases sending the electromagnetic signal to the excitation module 48. The ceasing of the electromagnetic signal causes the excitation module 48 to cease the release of the hydrating substance from the permeable member 44. The measurement module 46 continues to monitor the user's hydration level as long as the mouth guard 10 is inserted and powered on.

The measurement module 46 and the excitation module 48 can receive power from one or more batteries installed in the mouth guard 10. In some examples, the batteries are rechargeable. In some examples, the batteries are replaceable.

The mouthpiece 12 and the side lobes 14, including the dual module 42 and permeable member 44, can be included in a mouth guard kit. The individual components of the mouth guard kit are detachable and replaceable. For example, after using the mouth guard 10, the user can remove, for example, by unsnapping, the side lobes 14 from the mouthpiece 12 in order to, for example, wash the mouthpiece 12. The user can also remove the permeable member 44 from the mouthpiece 12. To insert the permeable member 44 into the dual module 42 using a snap fit, the user presses the permeable member 44 into the inner perimeter 40 of the ring of the dual module 42 to interlock the components. To remove the permeable member 44 from the dual module 42, the user pulls the permeable member 44 out of the ring of the dual module 42. The user can dispose of the used permeable member 44, and replace the used permeable member 44 with a new permeable member.

The mouth guard 10 can be made in various sizes. For example, the mouth guard 10 can be sized for youth, teens, and adults. The side lobes 14 can be made in appropriate sizes to correspond with the various sizes of the mouth guard 10. The mouth guard 10 can also be made with various levels of protective features. For example, the thickness and rigidity of the mouth guard 10 can depend on the activities that the mouth guard 10 is designed to be worn for. For example, the mouth guard 10 can be made with greater thickness and rigidity for wear while boxing, and with lesser thickness and rigidity for wear while playing tennis. The mouth guard 10 can be made with minimal thickness and rigidity for wear while sleeping or during a medical procedure.

Figure 9:
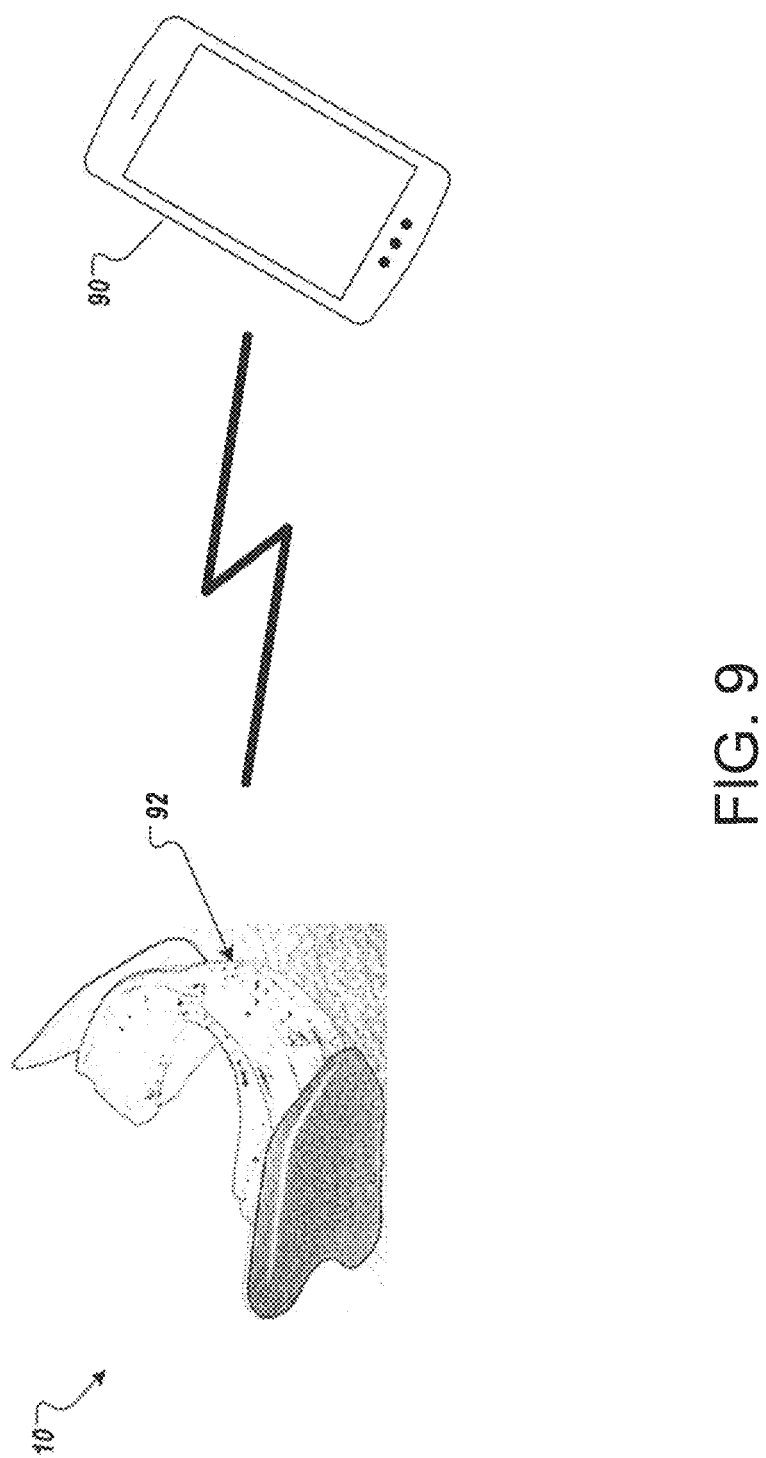
FIG. 9 is a diagram of an example hydrating mouth guard communicating with an external device.

Referring to FIG. 9, the mouth guard 10 can communicate with an external device 90. The external device 90 can be, for example, a mobile device such as a smart phone or a smart watch. The mouth guard 10 can communicate with the external device 90 through one or more radio frequency antennas 92 embedded within the mouth guard 10.

The user of the mouth guard 10, or a different user, for example, a coach or a parent, can use the external device 90 to control one or more functions of the mouth guard 10. For example, the user can use the external device 90 to remotely power the mouth guard on or off, or to remotely control the activation and deactivation of the hydrating substance release from the permeable member. In some examples, the mouth guard 10 can receive electrical power from the external device 90. For example, the mouth guard 10 can receive electrical power from the external device 90 through wireless charging.

Figure 10:
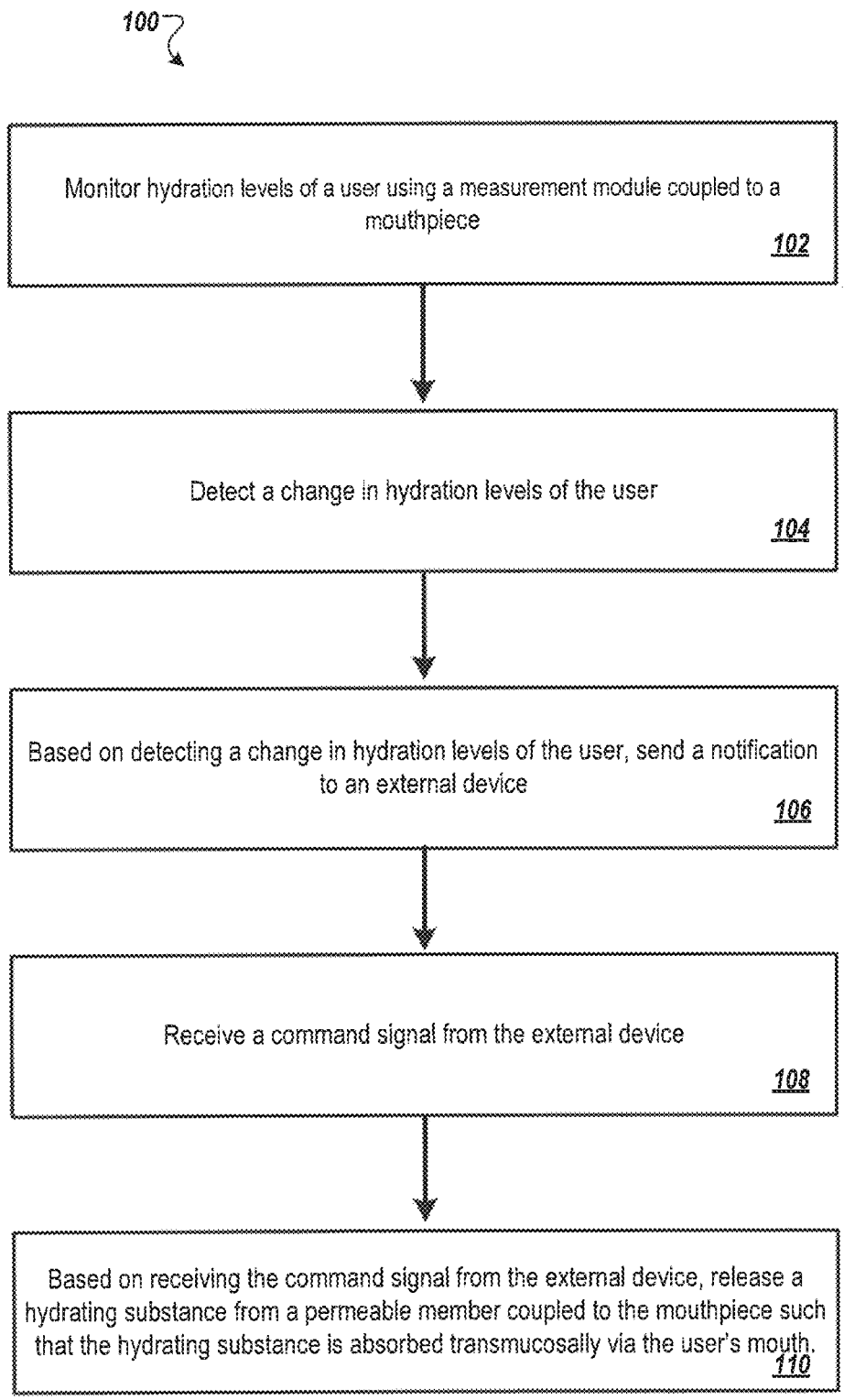
FIG. 10 is a flow diagram of a process for the hydrating mouth guard communicating with an external device.

Referring to FIG. 10, the process 100 for the hydrating mouth guard communicating with an external device includes monitoring the hydration level of a user using a measurement module coupled to a mouthpiece (102), and detecting a change in hydration level of the user (104). The mouth guard 10 can transmit data indicating the user's hydration level to the external device 90. The data can include the user's hydration level expressed, for example, as a percentage of a baseline level, or as a percentage of body composition.

The process 100 includes, based on detecting a change in hydration level of the user, sending a notification to an external device (106). For example, if the user's hydration level drops to a threshold body composition percentage, the mouth guard 10 can send a notification to the external device 90 indicating the drop in hydration. The notification can include a recommendation to remotely activate the hydrating substance release from the permeable member.

The process 100 includes receiving a command signal from the external device (108). The command signal can be, for example, a command signal to activate the hydrating substance release from the permeable member.

The process 100 includes, based on receiving a command signal from the external device, releasing the hydrating substance from the permeable member coupled to the mouthpiece such that the hydrating substance is absorbed transmucosally via the user's mouth (110).

The mouth guard 10 can send notifications to the external device 90 indicating the status of various components of the mouth guard 10. For example, the mouth guard 10 can send notifications indicating the time when the mouth guard 10 begins releasing the hydrating substance, and the time when the mouth guard 10 ceases releasing the hydrating substance. The mouth guard 10 can also send notifications indicating that a component such as the permeable member needs to be replaced, for example, due to containing low quantities of the hydrating substance.

The mouth guard 10 is designed to protect the teeth and supporting structures. The mouth guard 10 can be designed to achieve additional benefits as well. In some examples, the mouth guard 10 can be a neuromuscular mouthpiece that repositions the bite of the user to prevent the user from clenching the teeth. In some examples, the mouth guard 10 can be designed to position the jaw such that the user experiences a more open airway, improving oxygen exchange.

Figure 11:
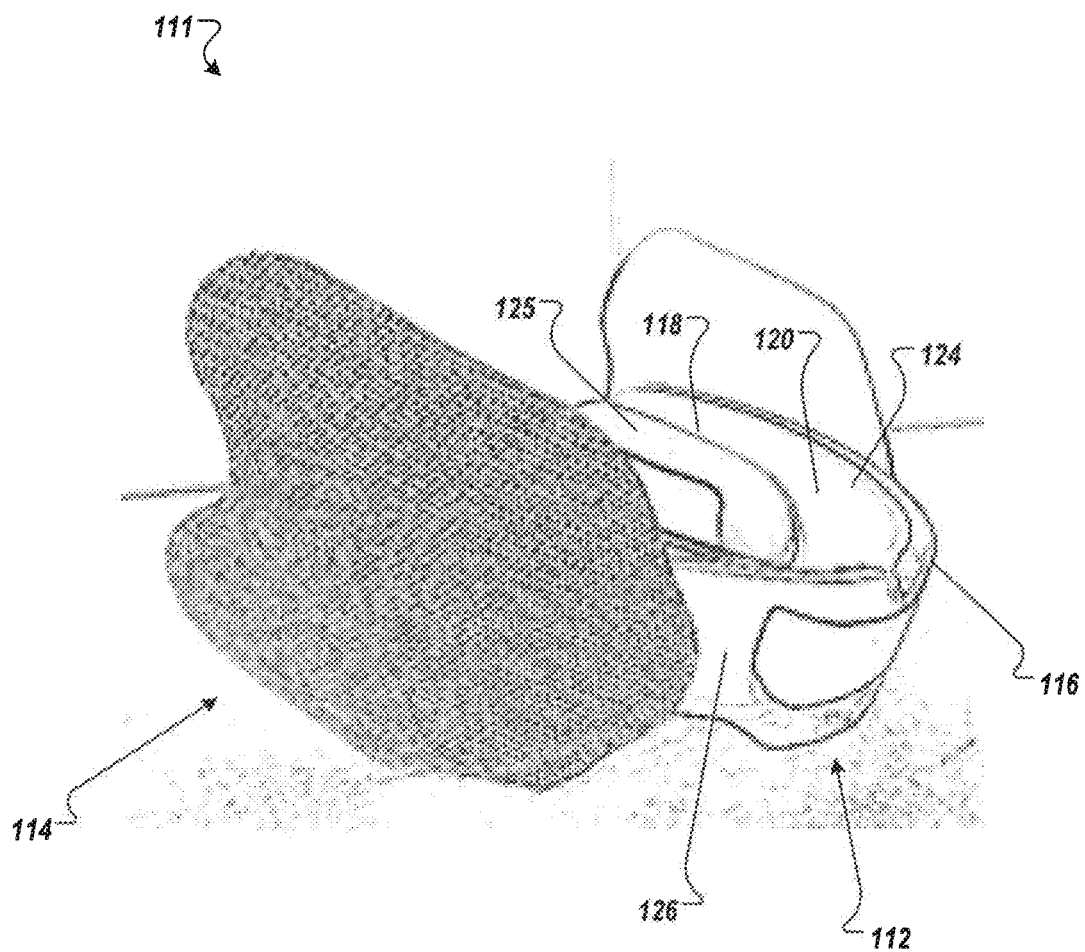
FIG. 11 is a diagram of an example hydrating mouth guard designed to fit on the top teeth only.

Referring to FIG. 11, a mouth guard 111 can be designed to fit on only the maxillary teeth, i.e., top teeth, of the user. The mouth guard 111 includes a U-shaped mouthpiece 112 designed to fit on a user's top teeth and two side lobes 114 attached to the mouthpiece 112 that, in use, are positioned against the buccosal tissue of the user's inner cheeks. The mouthpiece 112 includes an outer portion 126 having an outer surface 116, an inner portion 125 having an inner surface 118, and a mid-portion 124 having a top intervening surface 120. When worn by a user, the outer portion 126 covers the outer surfaces of the teeth with the outer surface 116 positioned facing the buccosal tissue. The inner portion 125 covers the surfaces of the teeth that face the tongue, and the top intervening surface 120 of the mid-portion 124 cover the grinding surfaces of the upper teeth.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Figure 7:
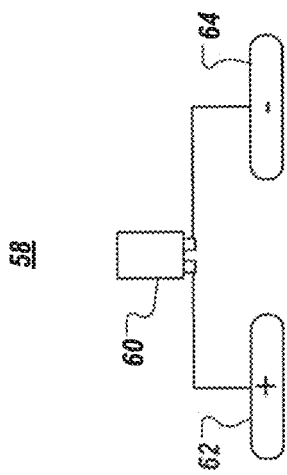
FIG. 7 is a diagram of an iontophoresis device.

The mouth guard 10 worn by the user 28 can also measure the user's blood glucose concentration and deliver an insulin solution to the user 28 via transmembrane diffusion. The dual module 42 includes a measurement module 46 for monitoring the blood glucose concentration of the user, and an excitation module 48 for inducing release of insulin solution from the permeable member 44. Referring to FIG. 7, the measurement module 46 and the excitation module 48 can each include one or more iontophoresis devices 58 for detecting a change in blood glucose concentration, and for driving a substance into the user's body tissue.

The process for delivering an insulin solution to the user 28 includes detecting a change in blood glucose concentration level of the user 28, and based on detecting the change in blood glucose concentration levels of the user 28, releasing the insulin solution from the permeable member 44 coupled to the mouthpiece 12 such that the insulin solution is absorbed transmucosally via the user's mouth.

The measurement module 46 can include a non-invasive blood glucose monitor for measuring blood glucose concentration. The non-invasive blood glucose monitor can be, for example, an iontophoresis device 58 functioning as a biosensor. The iontophoresis biosensor is described in Korean Patent No. KR100328654, hereby incorporated by reference in its entirety.

The iontophoresis device 58 can use reverse iontophoresis to conduct continuous extraction, sampling, and measurement of glucose in a biological system. In reverse iontophoresis, the current source 60 supplies a small electrical current, e.g., between 1 and 5 milliamperes, to the glucose-specific electrodes 62, 64. The current source 60 induces a voltage differential between the glucose-specific electrodes 62, 64 that are in contact with the user's body tissue. The charged glucose-specific electrodes 62, 64 attract glucose molecules from the body tissue through electroosmosis. The iontophoresis device 58 extracts and measures small amounts of the glucose, and compares the concentration of glucose to a reference concentration. For example, the reference concentration can be the user's baseline blood glucose concentration.

When the measurement module 46 detects a raised blood glucose concentration of the user, the measurement module 46 sends an electromagnetic signal to the excitation module 48. The signal stimulates the excitation module 48 to release the insulin solution from the permeable member 44 using sonication and iontophoresis.

To release the insulin solution using sonication, the nanosensor strips 66 within the excitation module 48 receive the electromagnetic signal from the measurement module 46, and transmit sonic energy to perform sonication on the permeable member 44. When agitated through sonication, the hydrogel releases the liposomes 45 containing the insulin solution through the membrane of the permeable member 44.

To deliver the insulin solution to the user's body using iontophoresis, the current source 60 of the iontophoresis device 58 within the excitation module 48 provides a small current to create a voltage differential between the glucose-specific electrodes 62, 64. The glucose-specific electrodes 62, 64 repel the liposomes 45 containing insulin, driving the liposomes 45 out of the permeable member 44 and into the user's body tissue. Iontophoresis increases the penetration, prolongs the release rate, and reduces the dispersal rate of the liposomes 45 within the body tissue. The iontophoresis process is described in U.S. Pat. No. 6,048,545, hereby incorporated by reference in its entirety.

Once released from the permeable member 44, the liposomes 45 release the insulin to the user's body tissues via transmembrane diffusion. The user's body tissues absorb the insulin, decreasing the user's blood glucose concentration.

The measurement module 46 continues to monitor the user's blood glucose concentration upon release of the insulin solution. When the user's blood glucose concentration lowers to reach a pre-determined level, the measurement module 46 ceases sending the electromagnetic signal to the excitation module 48. The ceasing of the electromagnetic signal causes the excitation module 48 to cease the release of the insulin solution from the permeable member 44. The measurement module 46 continues to monitor the user's blood glucose concentration as long as the mouth guard 10 is inserted and powered on.

In some examples, the mouth guard can send a notification to the external device 90 indicating a rise in blood glucose concentration. The notification can include a recommendation to remotely activate the insulin solution release from the permeable member 44.

In some examples, the mouth guard 10 can include a gum pad for mucoadhesive buccal dosage. The gum pad is described in U.S. Pat. No. 6,319,510, hereby incorporated by reference in its entirety. The gum pad is a laminate that includes a synthetic backing layer held in place on the gingiva, or gums, in the mouth, an intermediate reservoir layer for containing medication, and a semi-permeable outer layer facing outwardly toward oral mucosal tissues in the mouth. Saliva enters the semi-permeable outer layer and dissolves the medication in the reservoir layer into solution. The saliva-medication solution diffuses outwardly to the oral mucosal tissues. The gum pad can be used for the topical or systemic delivery of a wide range of pharmaceutical and nutritional agents, to include a hydrating substance or an insulin solution.

A user can wear the mouth guard 10 while participating in athletic activities, while sleeping, and during routine daily activities. The mouth guard 10 can be used before and during certain medical procedures, e.g., for pre-operative fluid and electrolyte management, as well as for an oral rehydration solution prior to general anesthesia procedures.

What is claimed is:
1. A transmucosal delivery device, comprising:
a mouthpiece configured for receipt on a user's teeth, the mouthpiece having an outer surface; and
a side lobe having an interior surface coupled to the outer surface of the mouthpiece and an exterior surface, the side lobe comprising:
a permeable member housing a hydrating substance to be delivered to the user through the user's oral mucosal tissue;
a measurement module for monitoring hydration of the user; and an excitation module for inducing release of the hydrating substance from the permeable member based on the monitored hydration;

wherein the exterior surface of the side lobe is configured to be positioned against the user's buccosal tissue for transport therethrough of the hydrating substance to the user's buccosal tissue.

2. The transmucosal delivery device of claim 1, wherein the mouthpiece is U-shaped, the mouthpiece comprising:

the outer surface;

an inner lingual surface; and an intervening occlusal surface.

3. The transmucosal delivery device of claim 2, further comprising: a dual module comprising the measurement module and the excitation module, wherein: the dual module is configured as a ring; and the dual module receives the permeable member within a perimeter of the ring.

4. The transmucosal delivery device of claim 3, wherein the dual module couples to the outer surface of the mouthpiece.

5. The transmucosal delivery device of claim 4, wherein the dual module is removably mounted to the mouthpiece.

6. The transmucosal delivery device of claim 1, wherein the permeable member is configured as a pouch housing the hydrating substance comprising a hydrogel.

7. The transmucosal delivery device of claim 6, wherein the hydrogel comprises liposome-entrapped hydration salts.

8. The transmucosal delivery device of claim 1, wherein the measurement module comprises one or more dielectric resonant oscillators.

9. The transmucosal delivery device of claim 1, wherein the excitation module comprises one or more nanosensor strips configured to receive electromagnetic energy and transmit sonic energy.

10. The transmucosal delivery device of claim 1, wherein the excitation module comprises one or more iontophoresis devices.

11. The transmucosal delivery device of claim 1, further comprising one or more antennas for transmitting or receiving signals.

12. The transmucosal delivery device of claim 1, further comprising a power receiving device configured to receive electrical power from a power source.

13. The transmucosal delivery device of claim 1, further comprising one or more batteries.

14. The transmucosal delivery device of claim 1, wherein the mouthpiece is configured for receipt on only the user's maxillary teeth.

15. The transmucosal delivery device of claim 1, wherein the mouthpiece is configured for receipt on the user's maxillary teeth and mandibular teeth.

16. The transmucosal delivery device of claim 1, wherein the side lobe is configured to span the user's buccosal tissue from below the user's mandibular gum line to above the user's maxillary gum line.

* * * * *